(12) United States Patent
Barbeau

(10) Patent No.: US 9,198,916 B1
(45) Date of Patent: Dec. 1, 2015

(54) COMPOUNDS AND METHODS FOR TREATING TUMORS

(71) Applicant: Donald L. Barbeau, Evanston, IL (US)

(72) Inventor: Donald L. Barbeau, Evanston, IL (US)

(73) Assignee: B&G Partners, LLC, Evanston, IL (US)

( * ) Notice: Subject to any disclaimer, the term of this patent is extended or adjusted under 35 U.S.C. 154(b) by 0 days.

(21) Appl. No.: 14/121,553

(22) Filed: Sep. 17, 2014

(51) Int. Cl.
*A61K 31/5415* (2006.01)
*A61K 31/675* (2006.01)
*A61K 45/06* (2006.01)

(52) U.S. Cl.
CPC .......... *A61K 31/5415* (2013.01); *A61K 31/675* (2013.01); *A61K 45/06* (2013.01)

(58) Field of Classification Search
CPC .......................... A61K 31/5415; A61K 31/675
USPC ........ 544/42; 546/202; 514/225.5, 225.2, 324
See application file for complete search history.

(56) References Cited

U.S. PATENT DOCUMENTS

| 3,239,514 | A | 3/1966 | Renz et al. | |
|---|---|---|---|---|
| 6,992,082 | B2 | 1/2006 | Finer et al. | |
| 8,088,918 | B2 * | 1/2012 | Barbeau | 540/557 |
| 8,623,864 | B2 | 1/2014 | Christensen et al. | |
| 2006/0035863 | A1 * | 2/2006 | Barbeau | 514/89 |
| 2014/0288060 | A1 | 9/2014 | Krappmann et al. | |

FOREIGN PATENT DOCUMENTS

| GB | 775279 | A * | 5/1957 |
|---|---|---|---|
| GB | 873316 | | 7/1962 |

OTHER PUBLICATIONS

Bylund "Interaction of Neuroleptic Metabolites with Dopaminergic, Alpha Adrenergic and Muscarinic Cholinergic Receptors" The Journal of Pharmacology and Experimental Therapeutics 1981 pp. 81-86 vol. 217 (1).
Yeh et al. "Trifluoperazine, an Antispycotic Agent, Inhibits Cancer Stem cell Growth and Overcomes Drug Resistance of Lung Cancer" American Journal of Critical Care 2012 pp. 1180-1188 vol. 186(11).
Sachlos et al. "Identification of drugs Including a Dopamine Receptor Antagonist that Selectively Target Cancer Stem Cells" Cell 2012 pp. 1-14 vol. 149.

* cited by examiner

*Primary Examiner* — Kahsay Habte

(57) ABSTRACT

The present invention relates to pharmaceutical compositions and methods for controlling tumor growth in cancer patients. These compounds and pharmaceutical compositions modulate the P-glycoprotein multidrug transporter system and inhibit the activated PI3K/Akt/mTOR/p70S6K signaling pathway. The compounds and pharmaceutical compounds of the present invention are particularly useful for treating metastatic and drug-resistant tumors.

19 Claims, 3 Drawing Sheets

Figure 2: Synthetic Scheme 1

COMPOUNDS AND METHODS FOR TREATING TUMORS

CROSS-REFERENCE TO RELATED APPLICATIONS

This patent application claims the benefit of prior filed provisional application No. 61/997,269 filed May 27, 2014, titled Compounds and Methods for Treating Tumors, which is hereby incorporated by reference in its entirety.

BACKGROUND OF THE INVENTION

Phenothiazines, phenazines and phenoxazines are selectively taken up by cancer cells in living, unfixed tissue, and have been used both for the demarcation of tumor cells within tissue and evaluated as agents for potentially treating cancer. One of the oldest of these compounds is methylene blue. Phenothiazine and thiothixene derivatives have been used as antipsychotic agents for over 60 years, and include the classical dopamine antagonists that preferentially bind to the family of dopamine receptors ($DR_{1-5}$). These phenothiazine-based dopamine receptor antagonists are among several types of so-called first generation antipsychotics which include chlorpromazine, fluphenazine, haloperidol, loxapine, mesoridazine, molindone, perphenazine, pimozide, thioridazine, thiothixene, and trifluoperazine that work by antagonism of dopamine ($D_2$) receptors throughout the brain. High levels of cardiotoxicity reported for phenothiazine-based dopamine receptor antagonists have unfortunately limited their clinical use in all but the most serious circumstances. Although phenothiazine-based dopamine receptor antagonists have considerable potential for their clinical utility outside of treating psychoses, the clinical use of these phenothiazine compounds is severely limited due to their dose-limiting toxicity. Thioridazine (Mellaril®), for example, was removed from the market because of its cardiotoxicity in patients, believed to be caused by the excessive prolongation of QT interval found, and a direct result of its high hERG liability.

Substituted phenothiazines such as those found in the first generation antipsychotics are tricyclic heteroaromatic lipophilic compounds having a planar aromatic ring structure with a cationic center disposed adjacent the ring nitrogen that provides the basis for dopamine receptor and cytochrome P450 binding. This particular chemical structure has proven to be valuable in treating tumors, which has been demonstrated for decades in numerous scientific reports. Phenothiazine compounds such as chlorpromazine, fluphenazine, thioridazine and promazine inhibit tumor growth in a number of cell systems both in vitro and in vivo. Various phenothiazine compounds have demonstrated selective and preferential uptake by the P-glycoprotein transporter (P-gp) that is overexpressed in tumor cells. Various phenothiazine compounds have also demonstrated inhibition of multiple protein kinases in the PI3K/Akt/mTOR pathway, restoration and enhancement of cytotoxicity toward drug-resistant tumors, inhibition of the rapid proliferation of cycling cells through control of DNA replication, mitotic arrest and accumulation of monopolar spindles (e.g. KSP/Eg5), activation of caspase-3, and activity against MRSA and intracellular methicillin-susceptible S. aureus (MSSA). It has also been reported that multidrug resistance can be modulated by phenothiazine compounds, and that phenothiazine compounds specifically modulate P-gp mediated drug transport (Wang et al. Basic Clinical Pharmacology and Toxicology 103(4): 336-341 (2008); Liu et al. Journal of the National Cancer Institute 89(20): 1524-1529 (1997); Tuyander et al. PNAS 101(43): 15364-15369 (2004); Lee et al. Cancer Research 67 (23): 11359-11367 (2007)).

A major problem in treating many cancers is tumor heterogeneity that prevents a complete cytotoxic response of cancer cells to any particular treatment; whether this resistance to therapy is an intrinsic characteristic of the cancer cell type or is acquired through genetic mutation, drug therapy or epithelial-to-mesenchymal transitions (metastases). Examples of intrinsically resistant tumors that have a genetic mutation include the $BRAF^{V600E}$ tumors found in metastatic melanoma cells. Drug-induced resistance can occur with conventional chemotherapy drugs such as doxorubicin and tamoxifen used in the treatment of breast cancer, and a number of drugs in other cancers. Metastatic tumor cells that have been transformed to mesenchymal-like tumor cells are generally resistant to conventional chemotherapy, are highly aggressive, and have unique biological and morphological characteristic that differ substantially from tumor cells in the primary tumor. While successful breast cancer treatments can control estrogen-positive tumor cells in primary tumors, they are unable to control estrogen-negative metastatic tumor cells. Finally, cancer initiating cells that are highly resistant to conventional therapies are often found in breast cancer as discrete populations of mammary cells have been isolated on the basis of cell-surface markers and a subpopulation of Lin-CD44+CD24−/Low cells. (Al-Hajj M, Becker M W, Wicha M, Weissman I and Clarket M F, Curr. Opin. Genet. Dev. 2004 February; 14(1):43-47; Sheridan et al. Breast Cancer Research 8: R59 (2006; Isom et al. Human Pathology 43(3): 364-373 (2012); Kawaguchi et al. Breast Cancer Symposium Abstract No. 40 American Society of Clinical Oncology (2010)).

Overcoming the resistance acquired by specific types of tumor cells is difficult because they generally have a high content of P-gp on their cell surface membrane. Phenothiazine-based compounds have demonstrated efficacy in treating epithelial, mesenchymal-type metastatic, solid and hematopoietic tumors containing stem cell-like (CD44+/ALDH+; CD133/ALDH+) populations as well drug-resistant tumor cells containing elevated levels of P-gp. Thioridazine has demonstrated the ability to inhibit the growth of tumor cells and inducing apoptosis without affecting the growth of normal cells (Byun H J et al. Microvascular Research 84: 227-234 (2012); Gil-Ad I et al. Oncology Reports 15: 107-112 (2006); Sachlos et al. Cell 149:1-14 (2012)).

The phosphatidylinositol 3-kinase (PI3K/Akt/mTOR) signaling pathway is a key regulator of physiological cell processes which include proliferation, differentiation, apoptosis, motility, metabolism, and autophagy. Aberrantly upregulated PI3K/Akt/mTOR signaling characterizes many types of cancers where it negatively influences prognosis. Cancer stem cells are more sensitive to PI3K/Akt/mTOR pathway inhibition in hematological and solid tumors with small molecules when compared to healthy stem cells (Georgescu et al. Genes & Cancer 1(12):1170-1177 (2011); Prochownik US 20100298352). Thioridazine and related phenothiazines have been reported to successfully inhibited phosphorylation of kinases upstream and downstream of Akt, including phosphorylation of PDk1, FOXO, Akt, mTOR1, mTOR2, 4E-BP1 and p70S6K. These reports suggest that thioridazine effectively suppresses tumor growth activity by targeting the PI3K/Akt/mTOR/p70S6K signaling pathway; however, phenothiazines are highly selective and do not inhibit the activation of EGFR, or extracellular signal-regulated kinase 1/2 (ERK1/2) (Choi et al Annals of the New York Academy of Sciences 1138: 393-403 (2008); William Sellers US Army Medical Research Grant W81XWH-04-1-0169 (2007 Report); Dhawan et al. Molecular Cancer Therapeutics 10(11) Supplement 1 Abstract A218 (2011); Kang et al. Apoptosis Mar. 30, 2012); Kau et al. Cancer Cell 4:463-476 (December 2003)).

Using suppression of pluripotency transcription factors such as Octamer 4 (Oct4), the phenothiazine compound thioridazine was reported to selectively target dopamine receptors on cancer somatic stem cells that are involved with the initiation of leukemic disease and on breast cancer cells. Treatment of these cancer somatic stem cells with thioridazine demonstrated cytotoxicity toward cancer stem cells while demonstrating no cytotoxicity to normal human pluripotent stem cells. (Sachlos et al. Cell 149:1-14 (2012)). The authors of this study speculated that because neoplastic pluripotent stem cells express dopamine receptors ($D_1$-$D_5$) and human pluripotent stem cells do not, this drug could selectively target cancer stem cells.

There is clearly a need for safer drugs that can be taken up by cancer cells, modulate the multidrug transporter system, inhibit the activated PI3K/Akt/mTOR/p70S6K signaling pathway, control cancer stem cells and safely control tumor growth, proliferation, differentiation, apoptosis, motility, or autophagy in patients.

It is an object of the present invention therefor to provide compounds useful for treating cancer patients that advantageously control therapy-resistant tumor cells and have low cardiotoxicity risk.

It is a further object of the present invention to provide compounds that modulate the P-glycoprotein transporter system, inhibit the activated AKT signaling pathway, and control tumor growth, proliferation, differentiation, apoptosis, motility, or autophagy in patients.

It is a further object of the present invention to modulate the P-glycoprotein transporter system, inhibit the activated AKT signaling pathway, and control tumor growth, proliferation, differentiation, apoptosis, motility, or autophagy in patients with cancer with noncardiotoxic phenothiazine compounds.

It is also an object of the present invention to provide a method for treating a subject in need of cancer therapy comprising administering to the subject a compound in an amount effective in inhibiting tumor growth, proliferation, differentiation, apoptosis, motility, or autophagy in patients.

BRIEF SUMMARY OF THE INVENTION

Figure 1:
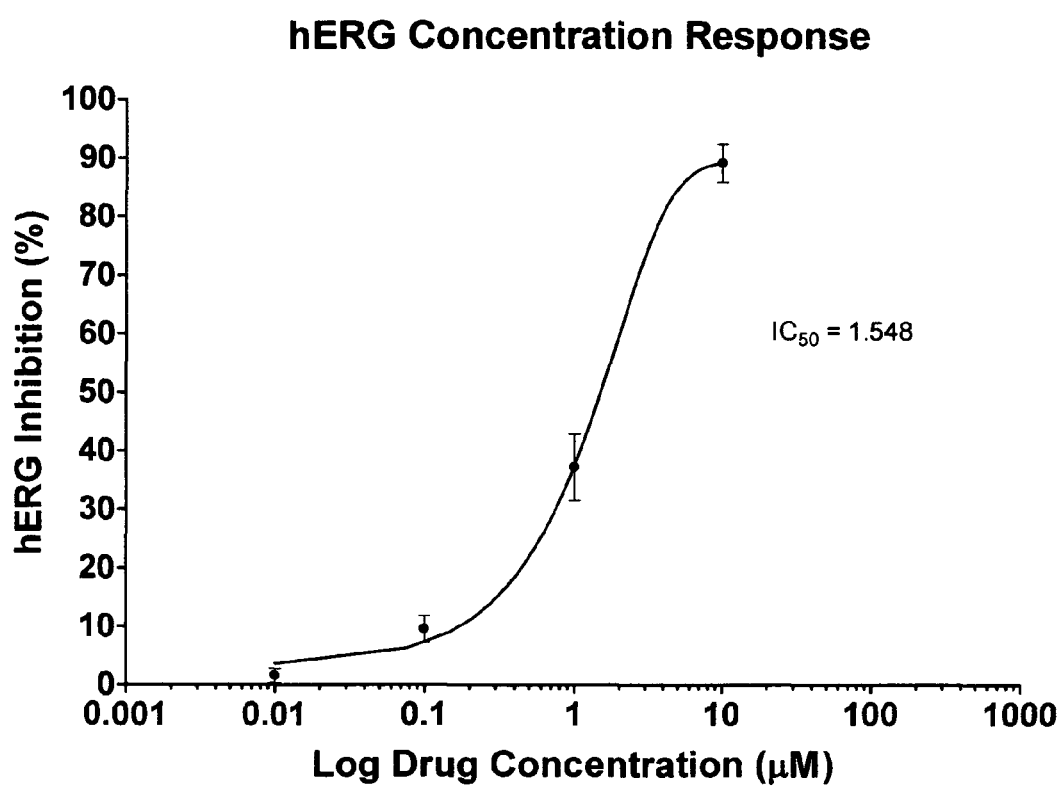
FIG. 1: hERG binding assay of 2-(methylsulfanyl)-10-[2-(piperidin-2-yl)ethyl]-10H-phenothiazine hydrochloride as described in Example 4.
Figure 2:
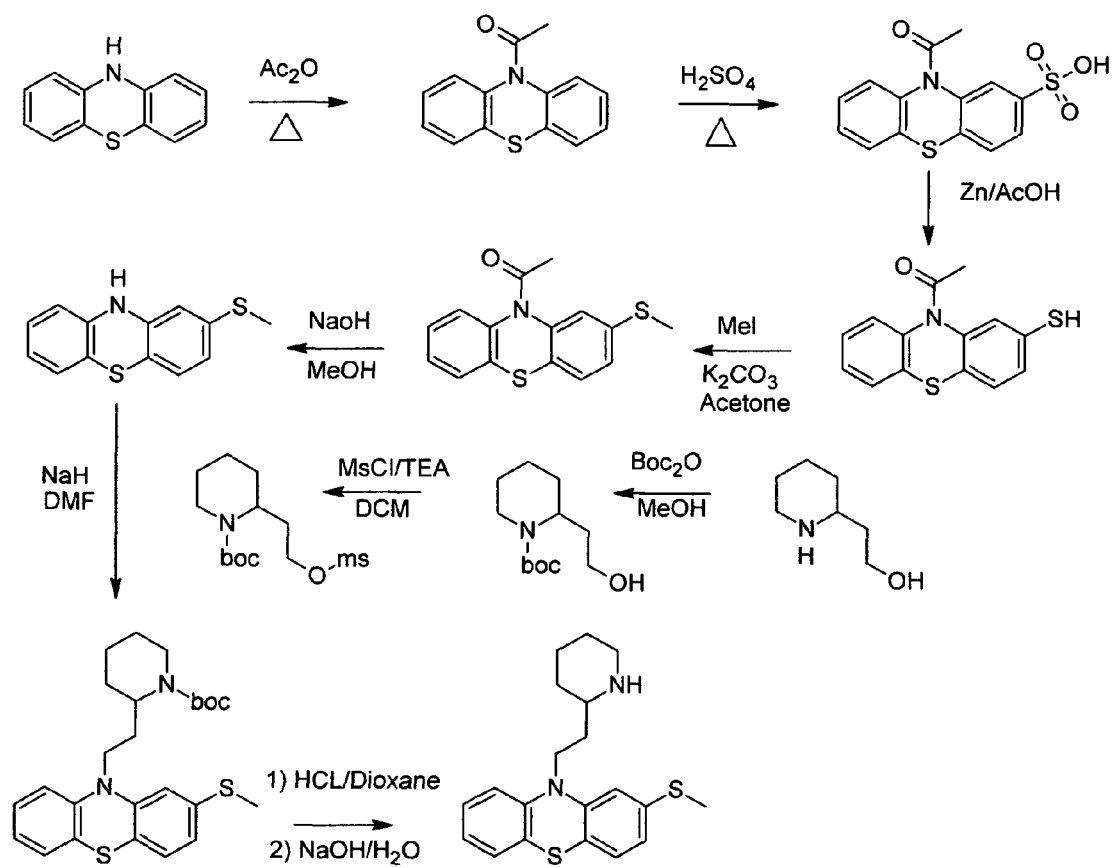
FIG. 2: Synthesis and preparation of compounds in accordance with the present invention.

The present invention relates to compounds and pharmaceutical compositions for treating a subject having a cancer in need of therapy thereof comprising administering to the subject a compound in an amount effective in inhibiting tumor growth, said compound having the formula

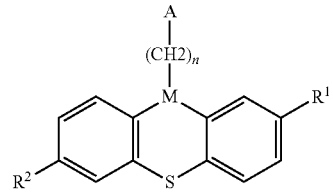

where A is selected from the group consisting of

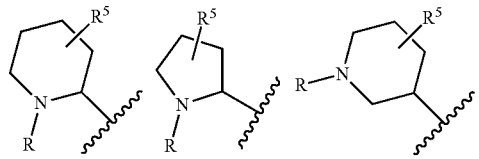

M is carbon or nitrogen, n is 2 or 3, $R^1$ is hydrogen, halogen, trifluoromethyl, sulfhydryl or an alkylthio group, $R^2$ is hydrogen, alkoxy or lower alkyl; R is hydrogen or a group having the formula $P(O)_3R^3R^4$, $R^3$ and $R^4$ are independently hydrogen or lower alkyl, $R^5$ is hydrogen or lower alkyl and pharmaceutically acceptable salts and prodrugs thereof in a pharmaceutically acceptable excipient, diluent or carrier. The compounds of the invention advantageously control therapy-resistant tumor cells and have low cardiotoxicity risk.

DETAILED DESCRIPTION OF THE INVENTION

In accordance with the present invention, provided are compounds having the formula

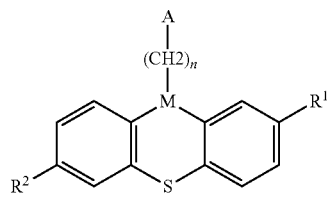

where A is selected from the group consisting of

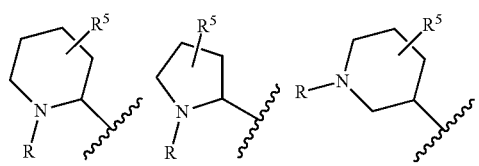

M is carbon or nitrogen, n is 2 or 3, $R^1$ is hydrogen, halogen, trifluoromethyl, sulfhydryl or an alkylthio group, $R^2$ is hydrogen, alkoxy or lower alkyl; R is hydrogen or a group having the formula $P(O)_3R^3R^4$, $R^3$ and $R^4$ are independently hydrogen or lower alkyl, $R^5$ is hydrogen or lower alkyl, with the proviso that when $R^2$ is hydrogen and $R^1$ is alkylthio, then A is selected from

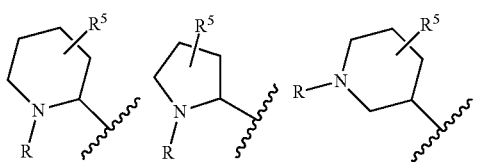 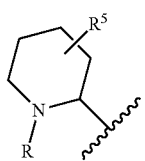

where R⁶ is lower alkyl, and pharmaceutically acceptable salts and prodrugs thereof.

In accordance with the present invention, $R^1$ is hydrogen, halogen, trifluoromethyl, sulfhydryl or an alkylthio group. In a preferred embodiment of the present invention, $R^1$ is an alkylthio group. In accordance with the present invention, the alkylthio group is a sulfone wherein the sulfonyl group is connected to an alkyl having from 1 to about three carbon atoms and also to a ring carbon. In a preferred embodiment of the present invention, the alkylthio is thiomethyl having the formula —S(CH$_3$).

In accordance with the present invention, "lower alkyls" are those alkyls containing a branched or straight chain acyclic alkyl group containing from one to five carbon atoms and include methyl, ethyl, propyl, isopropyl, butyl, isobutyl and pentyl. In accordance with the present invention, "alkoxy" groups include methoxy, ethoxy, propoxy such as n-propoxy, butoxy such as n-butoxy and t-butoxy, and pentoxy such as n-pentoxy.

In accordance with the present invention, $R^2$ is hydrogen, alkoxy or lower alkyl. In accordance with a preferred embodiment of the present invention, $R^2$ is hydrogen, methyl, ethyl or propyl. In one embodiment of the present invention, $R^2$ is preferably hydrogen. In another embodiment, $R^2$ is preferably methyl.

In accordance with the present invention, "halogens" are preferably fluorine and chlorine. In accordance with the present invention n is 2 or 3. In accordance with a preferred embodiment of the present invention n is 2. In accordance with the present invention M is carbon or nitrogen. In accordance with a preferred embodiment of the present invention M is nitrogen.

In accordance with the present invention, R is preferably hydrogen or a group having the formula $P(O)_3R^3R^4$. In accordance with one embodiment of the present invention, R is preferably hydrogen. In accordance with the present invention, $R^3$ and $R^4$ are independently hydrogen, methyl or ethyl. In accordance with a preferred embodiment of the present invention, $R^3$ and $R^4$ are both hydrogen.

In accordance with a preferred embodiment of the present invention, A is a group having the formula

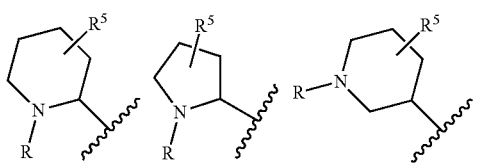

In accordance with the present invention, $R^5$ is hydrogen or lower alkyl. In accordance with a preferred embodiment of this invention when $R^5$ is a lower alkyl, $R^5$ is methyl or ethyl. In a more preferred embodiment of the present invention, $R^5$ is methyl. In accordance with a most preferred embodiment of the present invention, $R^5$ is hydrogen.

In one embodiment of the present invention, A can have the formula

In another embodiment of the present invention, such as when $R^2$ is hydrogen and $R^1$ is alkylthio A can have the formula where R⁶ is lower alkyl.

In accordance with the present invention, provided are compounds having the formula

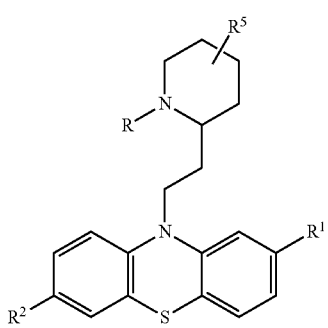

with the proviso that when $R^2$ is hydrogen and $R^1$ is alkylthio then $R^5$ is lower alkyl.

In accordance with a preferred embodiment of the present invention, provided are compounds having the formula with the proviso that when $R^2$ is hydrogen and $R^1$ is alkylthio then $R^5$ is lower alkyl.

In accordance with an alternate embodiment of the present invention, provided are compounds having the formula

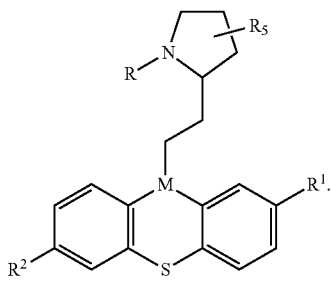

and compounds having the formula

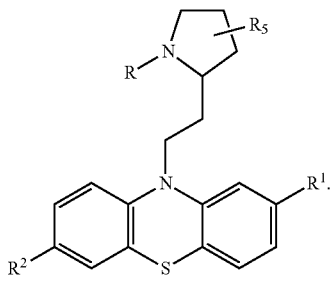

In accordance with another alternate embodiment of the present invention, provided are compounds having the formula

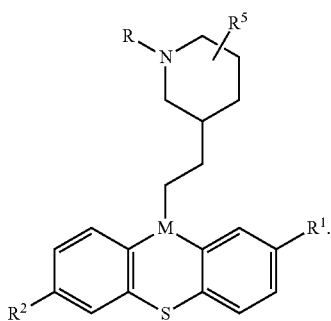

and compounds having the formula

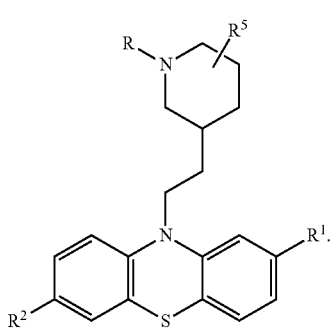

In accordance with a preferred alternate embodiment of the present invention, provided are compounds having the formula

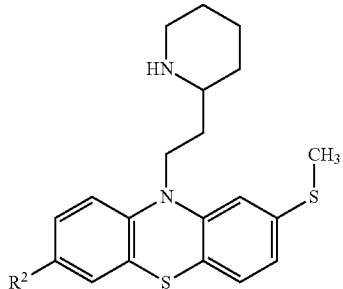

where $R^2$ is lower alkyl, and compounds having the formula

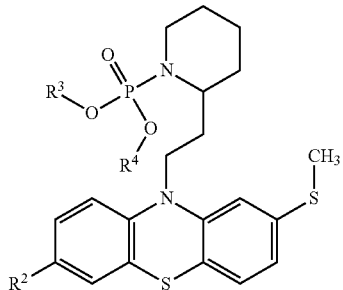

where $R^2$ is lower alkyl.

The compounds of the present invention advantageously control therapy-resistant tumor cells and have low cardiotoxicity risk. In accordance with the present invention, "control" of tumors includes inhibiting tumor growth, proliferation, differentiation, apoptosis, motility, or autophagy and the like in cancer patients.

The compounds of the present invention can be administered orally or by parenteral administration. In accordance with one embodiment of the present invention, the compounds are administered intravenously. In this embodiment, the presently claimed compounds provide an unexpected advantage over similar compounds in the prior art, particularly thioridazine. Thioridazine's cardiotoxicity in patients is believed to be caused by the excessive prolongation of QT interval (Hartigan-Go et al. *Clinical Pharmacology & Therapeutics* 60: 543-553 (1996), and a direct result of its high hERG liability. Surprisingly and unexpectedly, the compounds of the present invention have an advantage over previously used phenothiazine compounds like thioridazine because they have a low hERG liability.

In accordance with another embodiment of the present invention, the compounds of the present invention are administered orally. In this embodiment, the presently claimed compounds provide an additional unexpected advantage over similar compounds in the prior art, particularly thioridazine. Orally administered phenothiazines like thioridazine, for example, have demonstrated a propensity toward oxidation by cytochrome P450 2D6 enzymes to 7-hydroxy quinoneimine metabolites that have their oxidized (hydroxyl) group in the para-position to the ring nitrogen in the phenothiazine structure. Without being held to a particular theory or mechanism, we believe that the highly reactive quinoneimine toxicophores that are produced when phenothiazines-based drugs are administered orally are responsible in part for the proarrhythmic activity that has been reported to cause severe life-threatening arrhythmias (torsade de pointes) and sudden death. Compounds in which the highly reactive quinoneimine toxicophores are not produced provide a significant advantage over phenothiazines such as thioridazine In accordance with one preferred embodiment of the present invention, compounds are provided having the formula

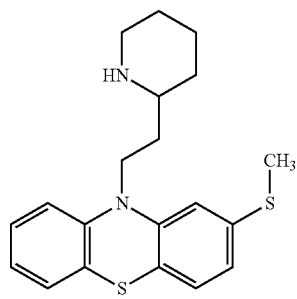

2-(methylsulfanyl)-10-[2-(piperidin-2-yl)ethyl]-10H-phenothiazine

These compounds can easily be prepared by a person skilled in the art, including the method as shown in the synthetic scheme or that described by Daniel et al. Pol. J. Pharmacol. 49(6):439-452 (1997); Daniel et al. Exp. Toxicol. Pathol. 51(4-5):309-314 (1999); Daniel et al. British Journal of Pharmacology 131: 287-295 (2000). Starting materials for compounds where $R^2$ is other than hydrogen, for example, include lower alkyls such as 3-methyl-10H-phenothiazine (CAS 3939-47-7), 3-ethyl-10H-phenothiazine (CAS 54027-87-1), 3-propyl-10H-phenothiazine (CAS 92-33-1), 3-butyl-10H-phenothiazine (CID 70288115), 3-propan-2yl-10H-phenothiazine (CID 70290282), 3-(1,1 dimethylethyl)-10H-phenothiazine (CAS 7678-79-7) and alkoxy such as 3-methoxy-10H-phenothiazine (CAS 1771-19-3).

The compounds of the present invention can be prepared as prodrugs that avoid biotransformation by cytochrome P450 2D6 to quinoneimine metabolites. The preparation of these prodrugs is described in U.S. Pat. No. 8,088,918 which is hereby incorporated by reference. In accordance with another preferred embodiment of the present invention, compounds are provided having the formula

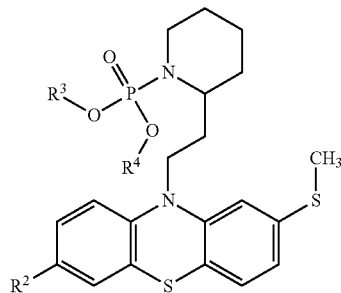

Other compounds that might avoid biotransformation by cytochrome P450 2D6 to quinoneimine metabolites include those with a lower alkyl group on the 7-position of the phenothiazine ring. Illustrated preferred compounds in this embodiment of the present invention include those having the formula

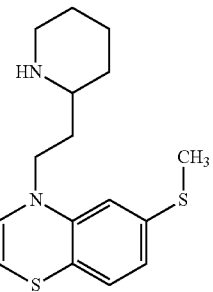

7-Methyl-2-methylsulfanyl-10-(2-piperidin-2-ylethyl)-10H-phenothiazine

The preparation and use of compounds and prodrugs in accordance with the present invention will be readily apparent to those skilled in the art and the well-known and well-documented procedures for substituted phenothiazine-based, thioxanthene and thiothixene-based drugs in the scientific and patent literature. The following United States patents provide illustrations on the synthesis of the phenothiazine analogs, and are hereby incorporated by reference in their entirety, together with the patents cited therein: U.S. Pat. No. 2,905,590; U.S. Pat. No. 3,310,553; U.S. Pat. No. 4,107,430; U.S. Pat. No. 4,042,695; U.S. Pat. No. 3,951,961; U.S. Pat. No. 6,407,231; U.S. Pat. No. 5,503,759; U.S. Pat. No. 3,305,547 and 8,088,918.

Preferred compounds in accordance with the present invention include:
2-Methylsulfanyl-10-(2-piperidin-2-yl-ethyl)-10H-phenothiazine;
7-Methyl-2-methylsulfanyl-10-(2-piperidin-2-yl-ethyl)-10H-phenothiazine;
2-Ethylsulfanyl-7-methyl-10-(2-piperidin-2-yl-ethyl)-10H-phenothiazine;
10-[2-(5-Ethyl-piperidin-2-yl)-ethyl]-2-methylsulfanyl-10H-phenothiazine;
10-[2-(5-Ethyl-piperidin-2-yl)-ethyl]-7-methyl-2-methylsulfanyl-10H-phenothiazine;
10-[2-(5-Ethyl-piperidin-2-yl)-ethyl]-2-ethylsulfanyl-7-methyl-10H-phenothiazine;
10-[2-(5-Methyl-piperidin-2-yl)-ethyl]-2-methylsulfanyl-10H-phenothiazine;
7-Methyl-10-[2-(5-methyl-piperidin-2-yl)-ethyl]-2-ethylsulfanyl-10H-phenothiazine;
2-Ethylsulfanyl-7-methyl-10-[2-(5-methyl-piperidin-2-yl)-ethyl]-10H-phenothiazine;
10-[2-(4-Ethyl-piperidin-2-yl)-ethyl]-2-methylsulfanyl-1 OH-phenothiazine;
10-[2-(4-Ethyl-piperidin-2-yl)-ethyl]-7-methyl-2-methylsulfanyl-10H-phenothiazine;
10-[2-(4-Ethyl-piperidin-2-yl)-ethyl]-2-ethylsulfanyl-7-methyl-10H-phenothiazine;
10-[2-(4-Methyl-piperidin-2-yl)-ethyl]-2-methylsulfanyl-10H-phenothiazine;
7-Methyl-10-[2-(4-methyl-piperidin-2-yl)-ethyl]-2-methylsulfanyl-10H-phenothiazine;
2-Ethylsulfanyl-7-methyl-10-[2-(4-methyl-piperidin-2-yl)-ethyl]-10H-phenothiazine;
7-Methoxy-2-methylsulfanyl-10-(2-piperidin-2-yl-ethyl)-10H-phenothiazine;
10-[2-(5-Ethyl-piperidin-2-yl)-ethyl]-7-methoxy-2-methylsulfanyl-10H-phenothiazine;
7-Methoxy-10-[2-(5-methyl-piperidin-2-yl)-ethyl]-2-methylsulfanyl-10H-phenothiazine;

10-[2-(4-Ethyl-piperidin-2-yl)-ethyl]-7-methoxy-2-methyl-sulfanyl-10H-phenothiazine; or 7-Methoxy-10-[2-(4-methyl-piperidin-2-yl)-ethyl]-2-methylsulfanyl-10H-phenothiazine.

Determining the dose and the amount of compounds effective in treating a subject having a disease and in need of therapy, controlling or reducing tumor growth or reducing tumorigenicity in accordance with the present invention will be readily apparent to those skilled in the art. In accordance with one aspect of the present invention, a method for treating a subject having cancer comprises administering to the subject a compound in an amount effective in modulating in vivo tumor growth or tumorigenicity.

The compounds of the present invention can be administered to cancer patients having therapy-resistant tumors including, but not limited to drug-resistant tumors, metastatic tumors and subpopulations of cancer stem cells. These types of tumors are found in patients with breast cancer, estrogen-negative breast cancer, triple-negative breast cancer, metastatic melanoma, pancreatic cancer, colon cancer, glioblastoma and lung cancer.

The compounds in accordance with the present invention have demonstrated highly potent in vitro cytotoxicity against drug-resistant tumors including the intractable metastatic melanoma tumors carrying the BRAF mutation, the locally invasive estrogen-negative breast tumors found in inflammatory breast cancer, and the highly invasive estrogen-negative breast tumors found in triple-negative breast cancer.

The compounds of the present invention can be administered alone or in combination with other cancer therapies. Compounds of the present invention can be administered to a patient receiving one or more chemotherapeutic or targeted therapies, where the compound is administered before, during or after the chemotherapeutic or targeted therapy. Illustrative therapies that can be combined with the compounds of the present invention include chemotherapeutic and targeted agents such as doxorubicin, tamoxifen, desleukin, dabradenib, dacarbazine, iplimumab, trametinib, interferon, dabrafenib, trametinib, vemurafenib, iplimumab, and the like.

The compounds of the present invention can be administered in admixture with a suitable pharmaceutical excipient, diluent or carrier selected with regard to the intended route of administration and standard pharmaceutical practice. The term "carrier" refers to diluents, excipients and the like for use in preparing admixtures of a pharmaceutical composition. For example, the compounds of the present invention can be administered orally in the form of tablets, capsules, multiparticulates, elixirs, solutions or suspensions, which may contain flavoring or coloring agents, either for immediate-, delayed-, modified-, sustained-, pulsed- or controlled-release applications. Suitable formulations of the compounds of the present invention may be in coated or uncoated form, as desired. Prodrugs in accordance with the present invention may be pH-labile and require delayed-release formulations to protect the prodrug from hydrolysis in the stomach. Preferably these delayed-release formulations contain enteric coatings.

Pharmaceutically acceptable carriers include but are not limited to sterile water, saline, buffered saline, dextrose solution, preferably such physiologically compatible buffers as Hank's or Ringer's solution, physiological saline, a mixture consisting of saline and glucose, and heparinized sodium-citrate-citric acid-dextrose solution and the like. As used herein, the term "pharmaceutically acceptable" means approved by a regulatory agency of the Federal or a state government or listed in the U.S. Pharmacopeia or other generally recognized pharmacopeia for use in animals, and more particularly in humans.

Unless otherwise specifically identified or claimed for preferred embodiments, the following general definitions are used in accordance with the present invention. In accordance with the present invention, the term "to target" or "to targeted" refers to the recognition of a target and delivery of a drug to that target; however, no internalization of the drug is inferred. In accordance with the present invention, the term "selectively target" refers to selective preference of one cell type over another. In accordance with the present invention, the term "modulate" refers to a change in the parameter measured, such that modulate can mean either an increase or decrease.

EXAMPLES OF THE INVENTION

Example 1

Preparation of 2-(methylsulfanyl)-10-[2-(piperidin-2-yl)ethyl]-10H-phenothiazine hydrochloride The hydrochloride of 2-(methylsulfanyl)-10-[2-(piperidin-2-yl)ethyl]-10H-phenothiazine was prepared in accordance with Synthetic Scheme 1. This compound had a pale blue color, a molecular weight of 365.55 g/mol, the positive ion mass [M+H$^+$] has an m/z of 357.15 and a purity of 98%.

Example 2

Preparation of 7-Methyl-2-methylsulfanyl-10-(2-piperidin-2-yl-ethyl)-10H-phenothiazine The hydrochloride of 7-Methyl-2-methylsulfanyl-10-(2-piperidin-2-yl-ethyl)-10H-phenothiazine is prepared in accordance with Synthetic Scheme 1 by substituting 3-methyl-10H-phenothiazine (CAS 3939-47-7) for phenothiazine.

Example 3

Preparation of 7-Methoxy-2-methylsulfanyl-10-(2-piperidin-2-yl-ethyl)-10H-phenothiazine The hydrochloride of 7-Methoxy-2-methylsulfanyl-10-(2-piperidin-2-yl-ethyl)-10H-phenothiazine is prepared in accordance with Synthetic Scheme 1 by substituting 3-methoxy-10H-phenothiazine (CAS 1771-19-3) for phenothiazine.

Example 4 hERG Binding Assays

The compound of Example 1 and positive control (E-4031 which selectively inhibits hERG current with an estimated IC$_{50}$=12 nM) concentrations were prepared by diluting stock solutions into a HEPES-buffered physiological saline (HBPS) solution (composition in mM): NaCl, 137; KCl, 4.0; CaCl$_2$, 1.8; MgCl$_2$, 1; HEPES, 10; Glucose, 10; pH adjusted to 7.4 with NaOH. All chemicals used in solution preparation were purchased from Sigma-Aldrich (St. Louis, Mo.) unless otherwise noted and were of ACS reagent grade purity or higher. Stock solutions of the compound of Example 1 and the positive control were prepared in dimethyl sulfoxide (DMSO) and stored frozen.

Stock solutions of the compound of Example 1 and control solutions contained 0.3% DMSO, and were sonicated (Model 2510/5510, Branson Ultrasonics, Danbury, Conn.) at room temperature for at least 20 minutes to facilitate dissolution.

The in vitro effects of the compound of Example 1 on the hERG (human ether-à-go-go-related gene) potassium channel current expressed in mammalian cells were evaluated at room temperature using the QPatch HT® (Sophion Bioscience A/S, Denmark), an automatic parallel patch clamp system. Recording of test results was performed in a glass-lined 96-well compound plate was loaded with the appropriate amounts of test and control solutions and placed in the plate well of the QPatch HT® (Sophion Bioscience A/S, Denmark).

The compound of Example 1 was evaluated at 0.01, 0.1, 1 and 10 µM, and each concentration was tested in six cells (n=6). The duration of exposure to each test article concentration was 3 minutes. A 0.5 µM sample of E-4031 was used to evaluate the sensitivity of the test system. The mean hERG inhibition of E-4031 was 90.3% (t 5.7 SD). The $IC_{50}$ of the compound of Example 1 is 1.548 µM.

Example 5

Repeated Dose Intraperitoneal (IP) BID Study in Mice

A total of 204.47 mg of the compound of Example 1 was weighed out in a sterile vial on an analytical balance, and a 10.22 ml volume of sterile DMSO containing 5% by volume sterile Tween 80 was added to the vial under a Class II sterile hood and mixed until fully dissolved to produce a 20 mg/ml stock solution of the compound of Example 1. The stock solution was split into 1.2 ml aliquots in sterile glass vials and stored frozen at −80° C.

Sterile 1.0 mg/ml injection solution of the compound of Example 1 was formulated in normal saline containing 4.75% DMSO and 0.25% Tween 80. A visible precipitate formed without the addition of at least 0.1% Tween 80. The injection solution was prepared by thawing one aliquot of sterile 20 mg/ml stock solution, and adding 0.526 cc of stock solution to a 10 ml sterile vial of USP 0.9% sodium chloride for injection (Hospira) to yield the desired concentrations of 1.0 mg/ml o the compound of Example 1, 4.75% DMSO, and 0.25% Tween 80. The injection solution was gently mixed until fully dissolved. Two 10 ml vials were prepared at a time, so the 1.2 ml stock solution aliquot did not need to be refrozen. Injection solution was stored at 4° C. for up to five days after preparation, after which it was considered expired and discarded.

A total of 16 female CD-1 mice with an age of approximately 8-10 weeks (25-30 g) were used in this repeated dosing study. Each animal was weighed on the days 1, 4, 8, 11, and 15 during treatment. A 10 mg/kg dose of the compound of Example 1 was provided by IP injection of 10 ml/kg of 1.0 mg/ml injection solution to each animal every 12.0±0.5 hr. The injection solution was removed from the refrigerator and allowed to warm at room temperature for several minutes. The septum of the injection solution was wiped with sterile alcohol, and animals received 10 ml/kg by individual insulin syringes (one syringe per animal per injection), with the injection volume calculated using the most recent weighing for each individual animal. IP injections were staggered between the left and right side of the abdomen from one dosing to the next. Animals were observed for behavior changes and monitored for adverse reactions at the injection site before each injection. The injection solution was returned to refrigerated storage after the last animal. Injections were performed in the morning (6:15-7:00 am) and evening (6:10-6:40 pm) each day until sample collection.

Plasma and selected tissues were collected from four mice at 30 min after the first injection on each specified collection date: evening of Day 1 (after injection 1), morning of Day 4 (after injection 6), morning of Day 8 (after injection 14), and morning of Day 15 (after injection 26). Animals were overdosed with carbon dioxide from a compressed gas cylinder at approximately 28 min after the last dose. They were left in the carbon dioxide until unresponsive, manual cervical dislocation was performed, and the animals were immediately exsanguinated via heart stick at 30 min after dosing. The whole blood from each animal was discharged into individual BD Microtainer $K_2$EDTA blood collection tubes, gently inverted to mix, and stored on ice. The brain, pancreas, and liver were then collected from each animal and stored on ice. Blood samples were centrifuged at 2500×g for 3 min, with the plasma withdrawn and placed in a microcentrifuge tube. Plasma samples were stored at −80° C. until LC-MS/MS analysis. Tissue samples were stored at −80° C.

LC-MS/MS analysis was performed using a Waters 2795 Separations Module, which includes an in-line mobile phase membrane degasser, quaternary solvent pumping system, a refrigerated autosampler, and a column oven with heater; a Micromass Quattro Micro LC/MS/MS triple quadrupole mass spectrometer with ESI probe; a Dell Optiplex 980 with 3.20 GHz Intel® Core™ i3 CPU, 1.18 GHz 3.42 GB RAM, running Microsoft Windows XP Professional, Version 2002, Service Pack 3. Instrument control and data analysis performed using Waters MassLynx V4.1 SCN683 software running on the Dell Optiplex 980 computer. Nano-pure water for LC-MS/MS (>18 MO-cm) was obtained using a Barnstead NANOpure Diamond Model D11931 water purification system.

A 1.0 mg/ml stock solution in methanol was prepared by weighing out 5.77 mg of the compound of Example 1 in a glass vial and adding 5.77 ml LC-MS grade methanol. This stock solution was stored at −80° C. and used for method development as well as in preparing plasma standards and quality control samples during plasma sample analysis.

A 10,000 ng/ml working solution of of the compound of Example 1 in methanol was prepared fresh before each LC-MS/MS analysis by adding 10.0 µl of 1.0 mg/ml methanol stock solution to 990 µl LC-MS grade methanol. For the preliminary plasma test sample analysis, the working solution of the compound of Example 1 was diluted to 3160, 1000, 316, 100, 31.6, 10.0, 3.16, 1.00, and 0.316 ng/ml in methanol. A 100 µl volume of each solution (including the 10,000 ng/ml solution) was placed in 1.5 ml microcentrifuge tubes. The methanol was evaporated in a vacuum centrifuge at 30° C., and 100 µl of blank commercial mouse plasma (PelFreez) was added to each tube. Tubes were heated in a 37° C. dry bath for 10 min, vortexed, and then kept on ice until analysis. For the full plasma test sample analysis, spiked plasma standards were prepared in the same manner, but at concentrations of 10000, 5000, 2500, 1000, 500, 250, and 100 ng/ml, and standards were resuspended in 100 µl blank plasma collected from study animals prior to the start of dosing.

Plasma standards, quality control (QC) samples, and study samples were all prepared for assay together for each analytical run. The sample preparation technique was adapted from the HPLC preparation method of Daniel et al. Pol. J. Pharmacol. 49(6):439-452 (1997); and Daniel et al. British Journal of Pharmacology 131: 287-295 (2000).

Study plasma samples were thawed on ice, vortexed, and 100 μl of each study sample to be assayed was added to 1.5 ml microcentrifuge tubes. Standards and QC samples were prepared in 100 μl plasma as already described. A 100 μl volume of chilled methanol (−20° C.) containing 2.5% by volume 5N NaOH was added to each tube to adjust the pH to 12 and precipitate/denature the plasma proteins. Tubes were vortexed, and 1000 μl of chilled n-hexane (−20° C.) containing 1.5% by volume isoamyl alcohol was added to each tube. Tubes were vortexed and stored at −20° C. overnight (about 16 hr). Tubes were then vortexed, centrifuged at 16,000×g for 60 sec, and 900 μl of supernate was transferred to a new tube. These tubes were vacuum centrifuged at 30° C. until dry, and 100 μl of 50% LC-MS grade acetonitrile:50% nano-pure water (>18 MD-cm) was added to each tube. Samples were heated on a dry bath at 37° C. for 15 min to aid solubilization, vortexed, stored in a refrigerator at 4° C. for 15 min to precipitate any remaining proteins, vortexed again, and centrifuged at 16,000×g for 60 sec to remove possible precipitates. Supernates were transferred to autosampler vials and stored at 4° C. until LC-MS/MS analysis.

An isocratic elution method was used with a flow rate of 0.30 ml/min and a mobile phase containing 45% LC-MS grade acetonitrile and 55% nano-pure water filtered through a 0.45 μm nylon membrane filter. Injections of 10 μl were made via the Waters 2795 auto sampler onto a Waters Atlantis 2.1 mm×50 mm-5 μm particle C18 column with a matching guard column for most method development tests and for the preliminary plasma study sample analysis. Elution was carried out on a Phenomenex Gemini 2.0 mm×50 mm-3 μm particle C18 column with matching guard column for the final plasma sample analysis. MS/MS detection was by multiple reaction monitoring (MRM) on the Micromass Quattro Micro LC/MS/MS triple quadrupole mass spectrometer. Total run time was 2 min per sample. The retention time of the compound of Example 1 was about 0.9 min on the Atlantis C18 column and about 0.6 min on the Gemini C18 column.

Figure 3:
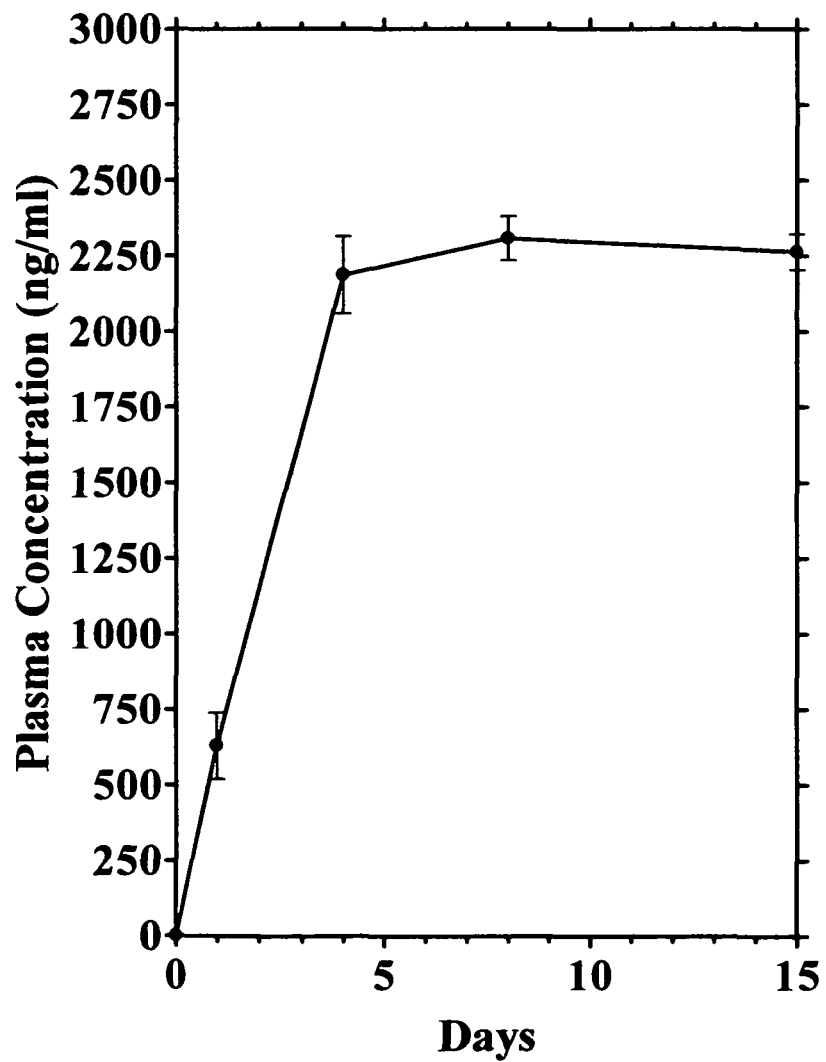
FIG. 3: Plasma concentrations of 2-(methylsulfanyl)-10-[2-(piperidin-2-yl)ethyl]-10H-phenothiazine hydrochloride from repeat dose intraperitoneal (IP) BID study in mice described in Example 5.

The results for the animals analyzed in both runs were averaged for the final pharmacokinetic (PK) analysis. The final average concentration of the compound of example 1 for each animal and a statistical summary of the values for each time point are provided in Table 1. A repeated-dose, single-compartment, first-order absorption model was then used to perform a nonlinear least-squares fit to the average measured plasma concentrations via an Excel Solver routine. The equation for the concentration ($C_N$) during any dosing interval (N) at time (t') after the most recent dose is given by $$C_N = \frac{FD}{V}\left(\frac{k_a}{k_a - k}\right)\left(\left[\frac{1 - e^{-Nk\tau}}{1 - e^{-k\tau}}\right]e^{-kt'} - \left[\frac{1 - e^{-Nk_a\tau}}{1 - e^{-k_a\tau}}\right]e^{-k_a t'}\right)$$

where $k_a$ is the absorption rate constant, k is the elimination rate constant, V/F is the apparent volume of distribution, D is the dose (10 mg/kg), and τ is the dosing interval (12 hr). A graph illustrating the average measured plasma concentrations at each time point is given in FIG. 3. The fitted values of the PK parameters represented by the optimal fit in FIG. 3 are 8.0 ml/g for the apparent volume of distribution, 0.48 hr for the absorption half-life, and 14.7 hr for the elimination half-life. The predicted plasma concentration range at steady state conditions is 1700-2600 ng/ml.

TABLE 1

Average measurement for each study animal, and statistical summary of concentration values at each time point.

| Day # | Injection # (N) | Plasma Concentration (ng/ml) for each study animal | | | | Plasma Concentration (ng/ml) for each time point | | | |
|---|---|---|---|---|---|---|---|---|---|
| | | 1 | 2 | 3 | 4 | Ave | sd | sem | CV (%) |
| 1 | 1 | 365 | 897 | 584 | 671 | 630 | 220 | 110 | 35 |
| 4 | 6 | * | 2442 | 2081 | 2037 | 2187 | 222 | 128 | 10 |
| 8 | 14 | 2153 | 2453 | 2411 | 2214 | 2308 | 147 | 73 | 6 |
| 15 | 28 | 2362 | 2352 | 2113 | 2223 | 2263 | 118 | 59 | 5 |

*Statistical outlier, not used in final results or PK itting

The present invention has been described in detail using specific examples to illustrate the preferred embodiments of the invention; however, it will be obvious to those skilled in the art that various modifications thereto can be made without departing from the spirit and scope thereof.

I claim:

1. A compound having the formula

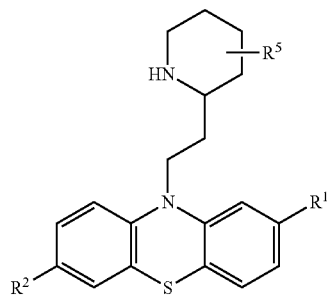

where $R^1$ is trifluoromethyl or an alkylthio group; $R^2$ is alkoxy or a branched or straight chain acyclic alkyl group containing from three to five carbon atoms; and $R^5$ is hydrogen or lower alkyl;

or the formula

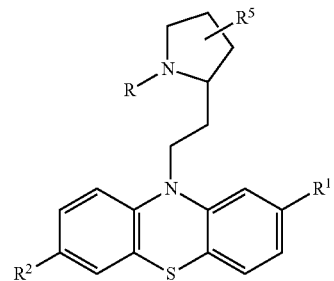

where $R^1$ is trifluoromethyl or an alkylthio group; $R^2$ is, alkoxy or a branched or straight chain acyclic alkyl group containing from three to five carbon atoms; R is hydrogen or a group having the formula $P(O)_3R^3R^4$, where $R^3$ and $R^4$ are independently hydrogen, methyl or ethyl; and $R^5$ is hydrogen or lower alkyl;

or the formula

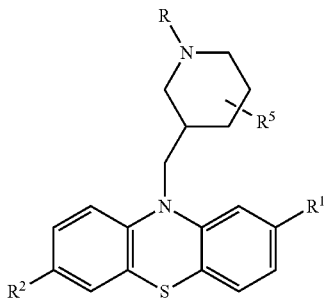

where R¹ is trifluoromethyl or an alkylthio group; R² is, alkoxy or a branched or straight chain acyclic alkyl group containing from three to five carbon atoms; R is hydrogen or a group having the formula $P(O)_3R^3R^4$, where $R^3$ and $R^4$ are independently hydrogen, methyl or ethyl; $R^5$ is hydrogen or lower alkyl; and pharmaceutically acceptable salts thereof.

2. A pharmaceutical composition comprising a compound having the formula

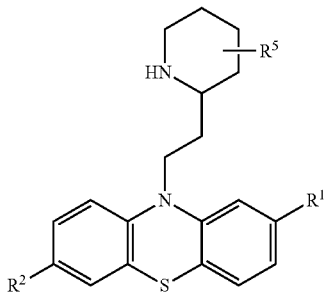

where R¹ is trifluoromethyl or an alkylthio group; R² is alkoxy or a branched or straight chain acyclic alkyl group containing from three to five carbon atoms and $R^5$ is hydrogen or lower alkyl;
or the formula

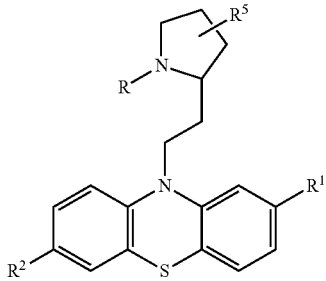

where R¹ is trifluoromethyl or an alkylthio group; R² is, alkoxy or a branched or straight chain acyclic alkyl group containing from three to five carbon atoms; R is hydrogen or a group having the formula $P(O)_3R^3R^4$, where $R^3$ and $R^4$ are independently hydrogen, methyl or ethyl; and $R^5$ is hydrogen or lower alkyl;

or the formula

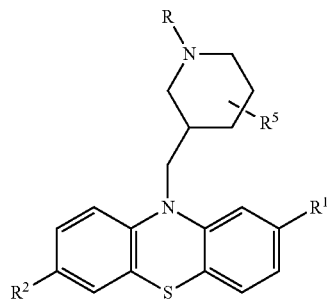

where R¹ is trifluoromethyl or an alkylthio group; R² is, alkoxy or a branched or straight chain acyclic alkyl group containing from three to five carbon atoms; R is hydrogen or a group having the formula $P(O)_3R^3R^4$, where $R^3$ and $R^4$ are independently hydrogen, methyl or ethyl; $R^5$ is hydrogen or lower alkyl; and pharmaceutically acceptable salts thereof, in a pharmaceutically acceptable excipient, diluent or carrier.

3. The pharmaceutical composition of claim 2 wherein the compound has the formula

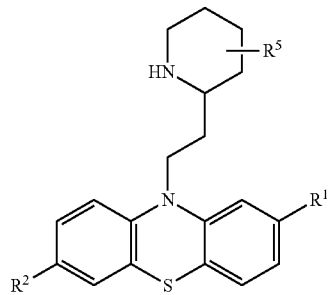

where R¹ is an alkylthio group.

4. The compound of claim 1 wherein R¹ is alkylthio.

5. The compound of claim 1 having the formula

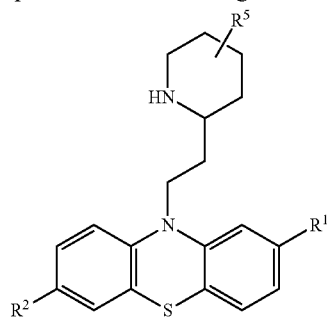

where R¹ is alkylthio.

6. The compound of claim 1 having the formula

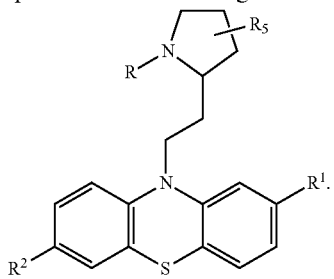

7. The compound of claim 1 having the formula

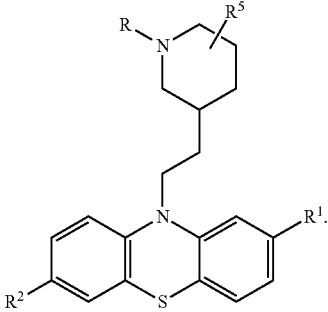

8. The compound of claim 5 having the formula

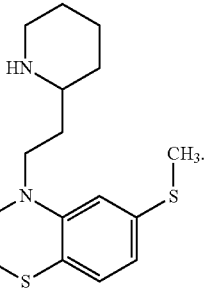

9. The compound of claim 5 having one of the following formula
- 7-Methoxy-2-methylsulfanyl-10-(2-piperidin-2-yl-ethyl)-10H-phenothiazine;
- 10-[2-(5-Ethyl-piperidin-2-yl)-ethyl]-7-methoxy-2-methylsulfanyl-10H-phenothiazine;
- 7-Methoxy-10-[2-(5-methyl-piperidin-2-yl)-ethyl]-2-methylsulfanyl-10H-phenothiazine;
- 10-[2-(4-Ethyl-piperidin-2-yl)-ethyl]-7-methoxy-2-methylsulfanyl-10H-phenothiazine; or
- 7-Methoxy-10-[2-(4-methyl-piperidin-2-yl)-ethyl]-2-methylsulfanyl-10H-phenothiazine.

10. A method for treating a subject having a cancer in need of therapy thereof comprising administering to the subject a compound in an amount effective in inhibiting tumor growth, wherein the subject in need of therapy has breast cancer, melanoma, pancreatic cancer, colon cancer, glioblastoma, hematopoietic cancer or lung cancer, said compound having the formula

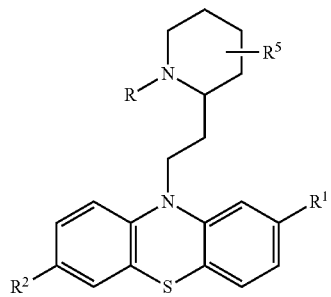

where $R^1$ is hydrogen, halogen, trifluoromethyl, sulfhydryl or an alkylthio group; with the proviso that when $R^1$ is alkylthio, that R is hydrogen;

or the formula

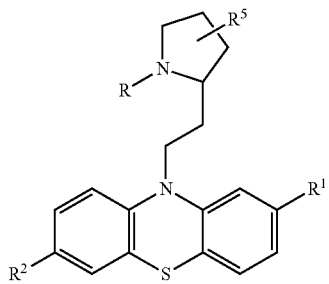

where $R^1$ is hydrogen, halogen, trifluoromethyl, sulfhydryl or an alkylthio group;
or the formula

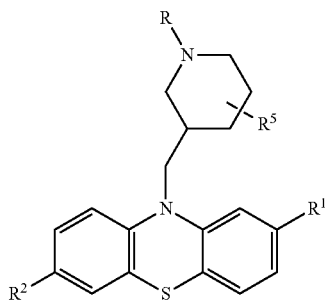

where $R^1$ is hydrogen, halogen, trifluoromethyl, sulfhydryl or an alkylthio group; $R^2$ is hydrogen, alkoxy or lower alkyl; R is hydrogen or a group having the formula $P(O)_3R^3R^4$, where $R^3$ and $R^4$ are independently hydrogen, methyl or ethyl; $R^5$ is hydrogen or lower alkyl, and pharmaceutically acceptable salts thereof in a pharmaceutically acceptable excipient, diluent or carrier.

11. The method of claim 10 wherein the compound has the formula

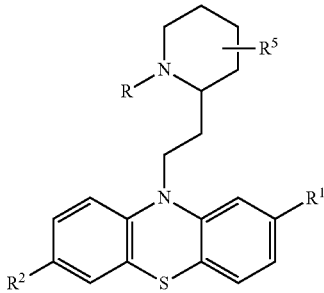

12. The method of claim 11 wherein said compound has the formula

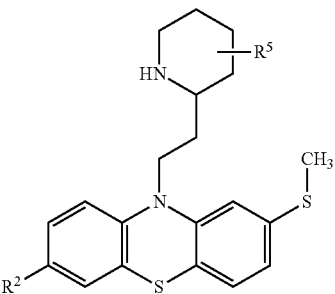

where $R^2$ is hydrogen or lower alkyl.

13. The method of claim 12 wherein said compound has the formula

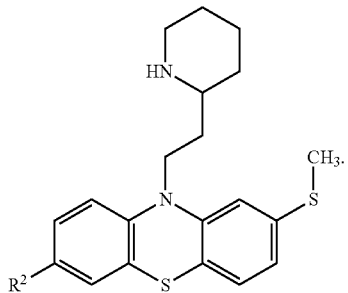

where $R^2$ is lower alkyl.

14. The method of claim 10 wherein said compound has the formula

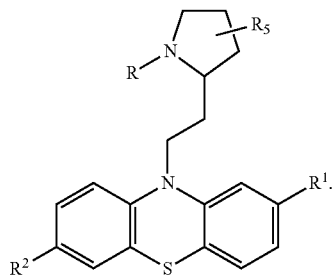

15. The method of claim 10 wherein said compound is administered to a patient receiving one or more chemotherapeutic or targeted cancer therapies, wherein said compound is administered before, during or after the chemotherapeutic or targeted therapy.

16. The method of claim 15 wherein said compound is administered to the patient after the chemotherapeutic or targeted therapy.

17. The method of claim 10 having one of the following formula

2-Methylsulfanyl-10-(2-piperidin-2-yl-ethyl)-10H-phenothiazine;
7-Methyl-2-methylsulfanyl-10-(2-piperidin-2-yl-ethyl)-10H-phenothiazine;
2-Ethylsulfanyl-7-methyl-10-(2-piperidin-2-yl-ethyl)-10H-phenothiazine;
10-[2-(5-Ethyl-piperidin-2-yl)-ethyl]-2-methylsulfanyl-10H-phenothiazine;
10-[2-(5-Ethyl-piperidin-2-yl)-ethyl]-7-methyl-2-methylsulfanyl-10H-phenothiazine;
10-[2-(5-Ethyl-piperidin-2-yl)-ethyl]-2-ethylsulfanyl-7-methyl-10H-phenothiazine;
10-[2-(5-Methyl-piperidin-2-yl)-ethyl]-2-methylsulfanyl-10H-phenothiazine;
7-Methyl-10-[2-(5-methyl-piperidin-2-yl)-ethyl]-2-ethylsulfanyl-10H-phenothiazine;
2-Ethylsulfanyl-7-methyl-10-[2-(5-methyl-piperidin-2-yl)-ethyl]-1 OH-phenothiazine;
10-[2-(4-Ethyl-piperidin-2-yl)-ethyl]-2-methylsulfanyl-10H-phenothiazine;
10-[2-(4-Ethyl-piperidin-2-yl)-ethyl]-7-methyl-2-methylsulfanyl-10H-phenothiazine;
10-[2-(4-Ethyl-piperidin-2-yl)-ethyl]-2-ethylsulfanyl-7-methyl-10H-phenothiazine;
10-[2-(4-Methyl-piperidin-2-yl)-ethyl]-2-methylsulfanyl-10H-phenothiazine;
7-Methyl-10-[2-(4-methyl-piperidin-2-yl)-ethyl]-2-methylsulfanyl-10H-phenothiazine; or
2-Ethylsulfanyl-7-methyl-10-[2-(4-methyl-piperidin-2-yl)-ethyl]-10H-phenothiazine.

18. The pharmaceutical composition of claim 2 comprising the compound in combination with a chemotherapeutic or targeted cancer drug.

19. A method for treating a subject having a cancer in need of therapy thereof comprising administering to the subject a compound in an amount effective in inhibiting tumor growth, wherein the subject in need of therapy has breast cancer, melanoma, pancreatic cancer, colon cancer, glioblastoma, hematopoietic cancer or lung cancer, said compound having the formula

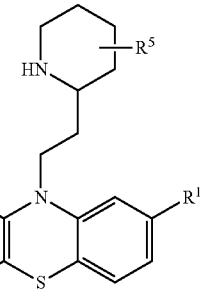

where $R^1$ is an alkylthio group, $R^2$ is hydrogen, alkoxy or lower alkyl, $R^5$ is hydrogen or lower alkyl; where the cancer contains mesenchymal-like tumor cells, tumor cells with $BRAF^{V600E}$ mutations, tumors with subpopulations of cancer-initiating cells, estrogen-negative breast cancer cells, or metastatic tumor cells with elevated levels of P-gp and an activated Akt signaling pathway; and pharmaceutically acceptable salts thereof in a pharmaceutically acceptable excipient, diluent or carrier.

* * * * *